United States Patent [19]
Andreiko et al.

[11] Patent Number: 5,464,349
[45] Date of Patent: Nov. 7, 1995

[54] ORTHODONTIC APPLIANCE PROVIDING FOR MESIAL ROTATION OF MOLARS

[75] Inventors: Craig A. Andreiko, Alta Loma; Mark A. Payne, Whittier, both of Calif.

[73] Assignee: Ormco Corporation, Glendora, Calif.

[21] Appl. No.: 286,000

[22] Filed: Aug. 4, 1994

Related U.S. Application Data

[63] Continuation-in-part of Ser. No. 973,973, Nov. 9, 1993.
[51] Int. Cl.$^6$ ...................................................... A61C 3/00
[52] U.S. Cl. ................................. 433/24; 433/8; 433/17
[58] Field of Search ........................... 433/8, 9, 16, 17, 433/20, 24

[56] References Cited

U.S. PATENT DOCUMENTS

| | | | |
|---|---|---|---|
| 3,477,128 | 11/1969 | Andrews | 433/24 |
| 3,660,900 | 5/1972 | Andrews | 433/24 |
| 4,511,331 | 4/1985 | Scebold et al. | 433/17 |
| 4,781,582 | 11/1988 | Kesling | 433/17 |
| 4,820,151 | 4/1989 | Pospisil | 433/17 |
| 5,011,405 | 4/1991 | Lemchem | 433/17 |
| 5,057,012 | 10/1991 | Kesling | 433/17 |
| 5,139,419 | 8/1992 | Andreiko et al. | 433/24 |
| 5,292,248 | 3/1994 | Schultz | 433/17 |

OTHER PUBLICATIONS

UNITEK, New Basic Edgewise Tubes, AMJO, vol. 49, No. 6, Jun. 1963.
Catalog: Ormco Orthodontic Products, pub. by Ormco Corporation, 1990, Sec. 1, 2 & 3.
Catalog: 3M Unitek Orthodontic Product, pub. by 3M, pp. 1-1 to 1-55 & 2-1 to 2-24.
Catalog: Rocky Mountain orthodontics Cat. #4, pub. by RMO, Inc., pp. E1-E62.
Catalog: Orthodontics pub. by Dentaurum, Inc., pp. 1-69.

*Primary Examiner*—Cary E. O'Connor
*Attorney, Agent, or Firm*—Wood, Herron & Evans

[57] ABSTRACT

An orthodontic bracket, preferably in the form of a buccal tube, is provided for connecting an orthodontic archwire to each mandibular first molar of a patient. The bracket has an archwire groove oriented to maintain the archwire at a positive rotation angle relative to the point on the surface of the molar at which the bracket is connected. The rotation angle is preferably approximately 2° for Caucasian patients and approximately 4° for Asian patients. The groove, while inclined to a positive (distal) rotation angle of greater than zero, may additionally be inclined mesially relative to the wire to account for smaller cross-sectional dimensions of the wire relative to the groove. In making a custom orthodontic appliance, a computer designs such buccal tubes with the grooves rotated to an angle optimally calculated for the patient. In the custom method, based on digitized tooth shape date for the patient, the embrasure of the upper first molars are placed perpendicular to an archform to occupy the least space on the arch, and the mesial buccal cusp and disto lingual cusp of each lower first molar is placed on a line coinciding with a line through the mesial marginal ridge and disto lingual groove of the upper first molar.

20 Claims, 5 Drawing Sheets

ORTHODONTIC APPLIANCE PROVIDING FOR MESIAL ROTATION OF MOLARS

This application is a continuation-in-part of pending U.S. patent application Ser. No. 07/973,973, filed Nov. 9, 1993, pending, entitled Method and Apparatus for Designing and Forming a Custom Orthodontic Appliance and for the Straightening of Teeth Therewith.

This application is related to the applicants' commonly assigned U.S. patent application, filed herewith, entitled "Low Profile Orthodontic Appliance".

1. Field of the Invention

The present invention relates to orthodontic appliances for straightening teeth, particularly to the components of the appliance, such as brackets or buccal tubes, that determine the relative positioning of the molars.

2. Background of the Invention

In current orthodontic practice, the teeth of patients are straightened through the use of orthodontic appliances typically formed of a pair of orthodontic archwires that are mounted on brackets, including slotted winged brackets or buccal tubes, each of which is secured to one of the individual teeth of the patient to support an archwire on the teeth.

An objective in orthodontic practice has been to provide an orthodontic appliance which, when attached to the teeth of the patient, will apply forces that urge the patient's teeth to their desired finish positions with a minimum amount of manipulation or "wire bending" by the orthodontist. This objective has been pursued by orthodontic appliance manufacturers in the design of better orthodontic appliances and by orthodontic practitioners in the selection and application of appliance components, such as the archwires, slotted brackets and buccal tubes. It has been recognized that the theoretically perfect appliance is one which is designed, selected and installed on the patient such that the archwire is elastically deformed, when installed on the teeth of the patient, so as to apply forces on each of the teeth, through the brackets and buccal tubes by which the archwire is connected to the teeth, in six degrees of freedom, causing the teeth to move until the stress in the wires is relieved, which occurs when the teeth are in their desired positions.

An optimum orthodontic appliance as set forth above must be a custom appliance specifically designed for the anatomy of the individual patient. Nonetheless, an appliance optimized to average anatomy may be employed to provide a minimum amount of manipulation by the orthodontist for the largest number of patients whose anatomy is close to the average.

Both custom and standard appliances present certain problems. In the treatment of the molars, for example, orthodontic appliances have usually been configured to connect the distal ends of the archwires to the teeth with brackets, usually in the form of buccal tubes, that are mounted on the surfaces of the teeth. The tubes are usually welded to pads that are bonded to the teeth or to bands that encircle the crowns of the teeth. Whether in the form of a buccal tube, in which a groove is provided in the form of a four sided bore of rectangular cross section in which an archwire is inserted, or in the form of a standard bi-wing bracket, in which a groove is provided in the form of a three sided rectangular slot in an archwire support, or other form of appliance component that mounts the wire to the teeth, the components have typically supported the wire receiving grooves in an orientation generally parallel to the tooth surfaces, that is, with no slot rotation. In one form of treatment known as the Roth method, molar brackets are provided with a slot or groove that is closer to the surface of the tooth at the mesial end than at the distal end to impart a desired distal or positive rotation to the tooth.

These brackets components for connection of the archwires to the molars, being the main structural anchor points of the appliance, have frequently been the reference with respect to which the geometries of the other appliance components have been designed. In the areas of the molars, however, the solutions of the prior art have been inadequate in meeting orthodontic ideals. While it has been recognized that upper molars, when optimally placed, are to occupy the least amount of mesial-distal space along the dental arch, such an objective has not been realistically achieved in the prior art. The additional realization that the molars are to occlude with certain cusps and ridges of the upper and lower molars in alignment, in combination with the tooth spacing consideration, has resulted in conclusions as to the desired molar rotations as set forth above. In the prior art, the molar placement criteria have not been effectively considered in a rigorous scientific manner that takes into account the anatomy of the teeth that includes the relationships among the prominences of the teeth that contact other teeth and the surfaces of the teeth on which the appliance components that support the archwire are to be mounted.

The present application is directed to a solution to a very compelling need that existed prior to the present invention by applicants for the improved design of orthodontic appliances in the areas of the molars.

SUMMARY OF THE INVENTION

In the emerging field of custom orthodontic appliance design and manufacture, it has been proposed by applicants, in their parent U.S. patent application Ser. No. 07/973,973, to digitize the shapes of the patient's teeth and jaw and to calculate an ideal occlusion in which the teeth of the specific patient will be placed in ideal finish positions. Based on these ideal calculated finish positions for the specific patient, a custom appliance is designed and manufactured automatically, based on the calculated occlusion, that move the patient's teeth to the ideal finish positions.

In their copending U.S. patent application entitled "Low Profile Orthodontic Appliance", applicants have provided an appliance that includes archwires of an optimal smooth shape supported on brackets that optimally space the wire from the teeth.

It is one objective of the present invention to provide a method of designing and producing a custom orthodontic appliance that improves the function of the appliance and the efficiency of the orthodontic treatment in relation to the molars.

It is a further objective of the present invention to provide a method that will improve the design and manufacture of standard orthodontic appliances that improve the positioning of the molars of a large percentage of patients with minimal bending of the archwires by the orthodontist.

It is a still further objective of the present invention to provide an orthodontic appliance and component thereof that will improve the function of both custom and standardized orthodontic appliances and the treatment of patients therewith.

In accordance with the principles of the present invention, an appliance is provided for the treatment of the teeth of the patient mesial, or anterior, of the molars, according to one of the accepted methods, or preferably, according to the custom orthodontic appliance performing method of applicants' parent application identified above. In the embodiment of the invention in which the applicants' custom appliance design and manufacturing method is used, the method of positioning the molars is performed simultaneously with, or in an interactive method along with, the custom design of the other portions of the appliance. In other embodiments of the invention used with other accepted appliance design methods, the present invention is used to design slotted brackets and buccal tubes for attachment to the molars that interface with the distal extension of the archwire of the appliance to optimally interface the appliance with the molars, and to optimally position the molars thereby.

According to the preferred embodiment of the present invention, in the design of the appliance, the finish positions of the upper molars are set so that the molars occupy minimal space on the dental arch and to optimally occlude with the molars of the opposing arch. Preferably, the upper first molars are placed first to contact the tooth mesial thereto with the embrasure of the molars generally tangent to the distal surface of the adjacent tooth. Then, a measurement is made of the angle between the archform and a line through the mesial marginal ridge and the disto-lingual cusp of the maxillary first molar. Next, the rotation of the mandibular first molar is calculated such that a line through the mesial buccal cusp tip and distal lingual groove of the mandibular first molar is at the angle measured for the maxillary first molar as explained above. The mandibular first molar is then placed on a distal extension of the archform, that is, with the mesial buccal cusp tip of the lower first molar in line with the buccal cusp tips of the lower bicuspids. Then, the lower second molars are placed with their buccal cusp tips in line on the same archform, and the upper second molars are placed with their appropriate prominences in occlusion with the corresponding features of the lower molars. As used here, the term "placed" refers to the calculations of position performed by mathematical modeling in a computer, preferably in accordance with applicants' custom orthodontic appliance design system of the parent application referred to above.

Based on applicants' tooth placement method and consideration of tooth anatomy, applicants have provided for the wire receiving grooves, that is the bracket slots or buccal tubes, of on the lower first molar for most patients, particularly Asian patients, that is farther from the tooth at the mesial end than at the distal end, to thereby rotate the molar in the mesial or negative direction relative to the archwire. The tooth rotation is preferably approximately 2° in Caucasian patients and approximately 4° in Asian patients.

The present invention positions the molars in more nearly ideal positions than appliances of the prior art, and facilitates the design and provision of a superior all around orthodontic appliance than does the prior art. The invention further reduces the need for wire bending and other adjustments to the appliance by the orthodontist.

These and other objectives and advantages of the present invention will be more readily apparent from the following detailed description of the drawings and preferred embodiments, in which:

DETAILED DESCRIPTION OF THE PREFERRED EMBODIMENTS

Figure 1:
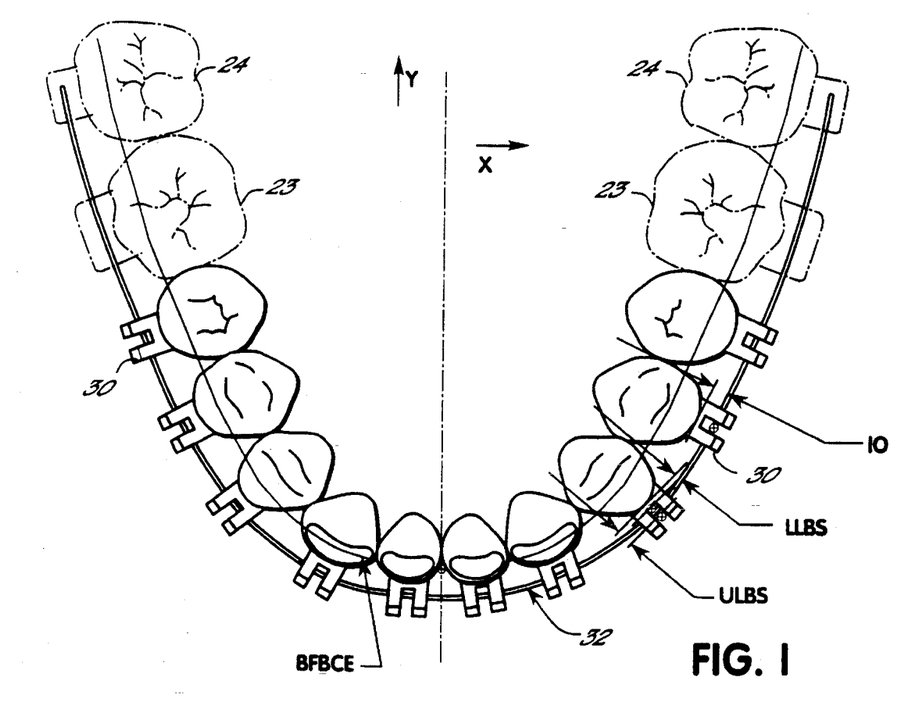
FIG. 1 is a plan diagram of a mandibular archform of teeth of a patient from the incisors to the bicuspids arranged in ideal finish positions as preferred by the present invention.

According to one preferred embodiment of the present invention, a custom orthodontic appliance is designed and manufactured, with the aid of a specially programmed digital computer, to provide brackets, for example in the form of buccal tubes, for the upper and lower first molars. Preferably, the design and manufacture of the portion of the appliance that includes the brackets for the more teeth mesial to the molars is carried out according to the method described in the applicants' U.S. patent application Ser. No. 07/973,973, filed Nov. 9, 1993, entitled Method and Apparatus for Designing and Forming a Custom Orthodontic Appliance and for the Straightening of Teeth Therewith, expressly incorporated by reference herein, and of which this application is a continuation-in-part. In accordance the parent application, preferred finish positions for the mandibular teeth from the incisors to the bicuspids are calculated such that the mandibular teeth are arranged in an ideal archform as illustrated in FIG. 1 with the incisal tips of the lower incisors and cuspids and the buccal cusp tips of the lower bicuspids lying in a smooth mathematically definable curve which applicants refer to as the Best Fit Buccal Cusp Equation, or BFBCE. The calculations are based on digitized data of the shape of the teeth and jaw of the individual patient.

Figure 2:
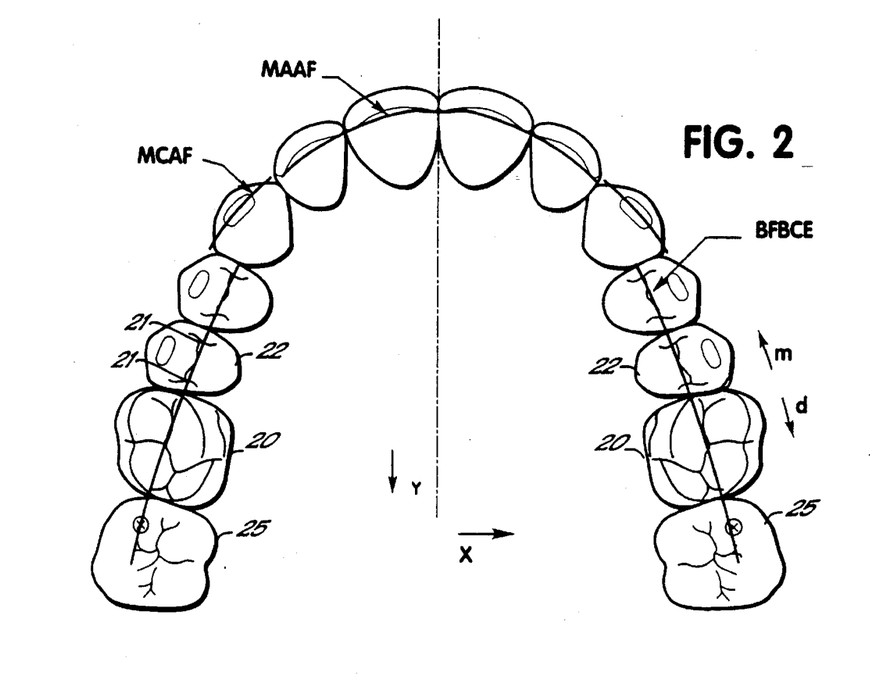
FIG. 2 is a plan diagram of a maxillary archform of teeth of a patient from the incisors to the bicuspids arranged in ideal finish positions to occlude with the lower teeth arranged as in FIG. 1 and including the upper first molars positioned in accordance with one preferred embodiment of the present invention.

Further in accordance with the method of the parent application, ideal finish positions are also calculated for the upper teeth of the patient, which place the upper teeth of the patient relative to the BFBCE for the lower teeth. In accordance with these calculated positions, the tips of the maxillary incisors lie on a maxillary archform MAAF that is spaced from the BFBCE a distance that takes into account the thicknesses of the upper and lower teeth, proper overlap of the upper and lower teeth, and proper clearance between the upper and lower teeth. The upper bicuspids are positioned so that the intersections of their central grooves and mesial marginal ridges lie on the BFBCE to thereby occlude with the cusps of the lower teeth. The tips of the upper cuspids are placed on a curve MCAF between the tips of the upper laterals and the buccal cusp tips of the upper first bicuspids, as illustrated in FIG. 2.

Figure 16:
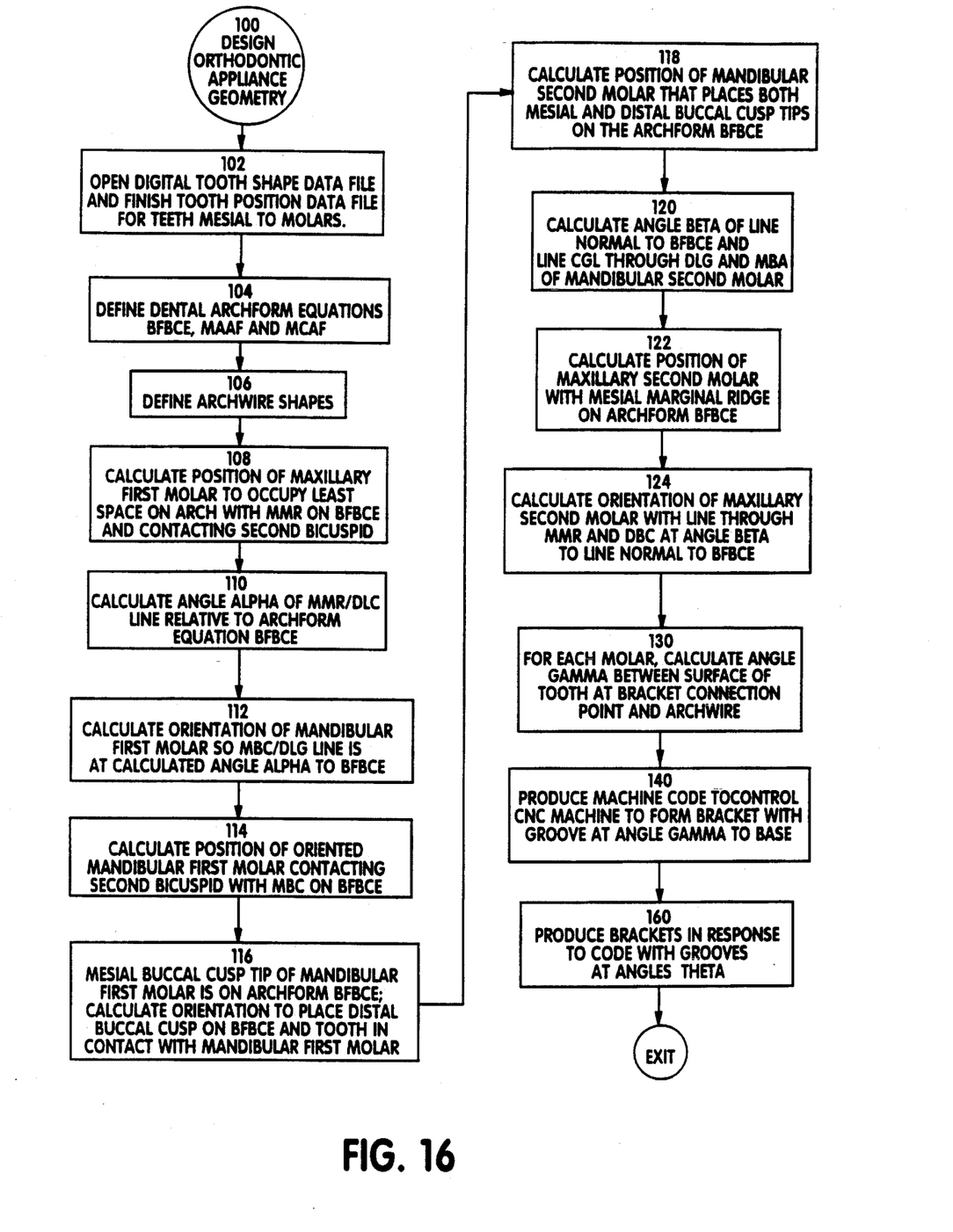
FIG. 16 is a flowchart illustrating the computer aided design and manufacture of a custom orthodontic appliance including the bracket of FIG. 15.

Whether the method of the parent application is used or some other method of determining the ideal placement of the incisors through the bicuspids of the patient, the finish positions of the teeth will include finish positions of the more distal teeth, generally the second bicuspids, with buccal cusps of the lowers, and the central grooves of the uppers, that may be considered to lie on an archform that passes through a similar feature of the mesially adjacent tooth. In addition, an appliance design will be established that includes an archwire, which will mount on brackets on the teeth and can be extended to lie in a fixed position adjacent the molars. In accordance with certain principles of the present invention, the finished positions of the molars are determined, from digitized data in a digital computer, by an extension of the method of the parent patent application referred to above, as set forth below, which is preferably carried out in a digital computer programmed in accordance with the flowchart of FIG. 16. The numbers in parentheses below refer to steps illustrated in the flowchart.

Figure 3:
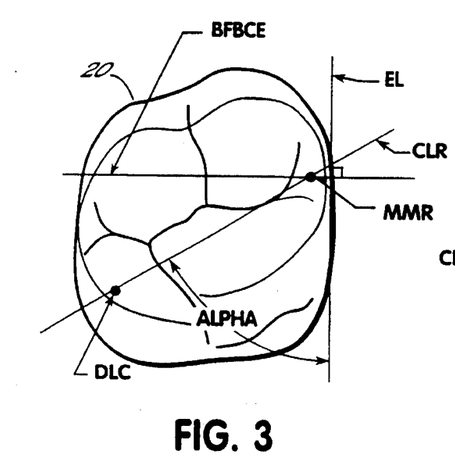
FIG. 3 is a plan diagram illustrating the parameters for placing the maxillary first molar in accordance with the embodiment of FIG. 2.

Preferably, the method (100) begins with (102) provision of digitized tooth shape data, finish positions for the teeth mesial to the molars, (104) definition of the archforms for the teeth and (106) definition of the archwire shapes, as set forth above. Then, (108) an occlusion is constructed by the digital calculation of the placement positions of the maxillary and mandibular first molars, beginning with the maxillary first molar 20. This is accomplished by establishing the finish positions of the maxillary first molars 20 on an archform, preferably the BFBCE described above, or onto a similar archform through the central groove and marginal ridge intersection points 21 on the immediately adjacent bicuspid 22, as further illustrated in FIG. 2. This involves the construction, for this tooth, of a line parallel to the embrasure EL, and rotating the molar until the embrasure line EL is normal to the BFBCE, as illustrated in FIG. 3. So positioned, the upper molar will occupy the least amount of space in the arch. Next a line CRL between the distal lingual cusp DLC and the mesial marginal ridge MMR is constructed for the tooth. Then (110) an angle ALPHA between the line EL and the line CRL is the calculated. The position of the first upper molar 10 is determined as the position that places the MMR on the BFBCE with the line EL perpendicular to the BFBCE.

Figure 4:
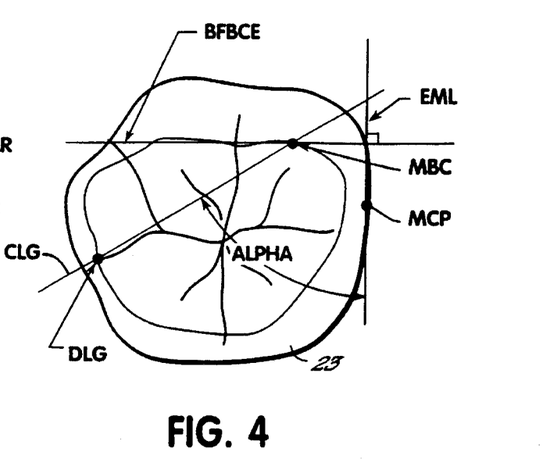
FIG. 4 is a plan diagram illustrating the parameters for placing the mandibular first molar in accordance with a preferred embodiment of the invention.
Figure 5:
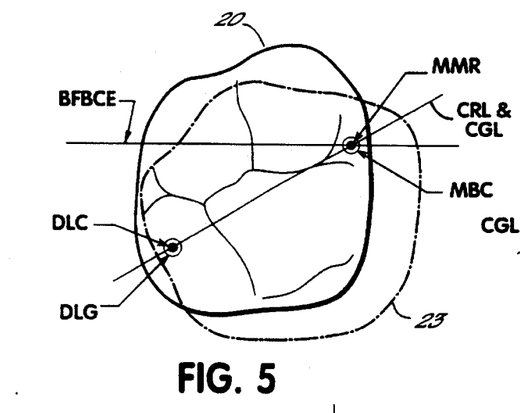
FIG. 5 is a first molar occlusalgram illustrating the relationship of the molars of FIGS. 3 and 4.

Then, the finish position of the lower first molar 23 is determined, as illustrated in FIG. 4, (112) by construction of a line CLG between the mesial buccal cusp MBC and the disto lingual groove DLG for the tooth. A line EML is constructed for the tooth at the angle ALPHA through the mesial buccal cusp MBC. The molar 23 is rotated about the mesial buccal cusp MBC and (114) translated along the BFBCE until (116) the line EML is normal to BFBCE and the mesial contact point MCP of the molar 23 is positioned appropriately. The resultant occlusalgram is presented in FIG. 5.

Figure 6:
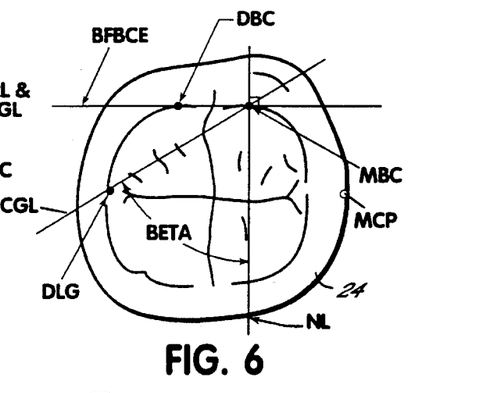
FIG. 6 is a plan diagram illustrating the parameters for placing the mandibular second molar in accordance with the preferred embodiment of the invention.

Next, the finish positions of the maxillary and mandibular second molars are determined. As with the first molars 20 and 23, the second molars are positioned with respect to an archform that may be represented by an equation through the buccal cusp tips of the lower bicuspids and the central-groove/marginal-ridge intersections of the upper bicuspids. This equation is preferably the BFBCE described above. The finish position of the mandibular second molar 24 is determined first. By definition in the finish position calculating process described in the parent application identified above, the mesial buccal cusp tip MBC of the mandibular second molar 24 is on the Best Fit Buccal Cusp Equation BFBCE. Referring to FIG. 6, (118) the mandibular second molar 24 is rotated about its mesial buccal cusp tip MBC and translated along the BFBCE until its distal buccal cusp tip DBC is located onto the BFBCE and the mesial contact point MCP is positioned appropriately. A line NL normal to the BFBCE through the mesial buccal cusp tip MBC is constructed for the tooth. Then, (120) an angle BETA between the line NL and line CGL between the distal lingual grove DLG and the mesial buccal cusp MBC is calculated.

Figure 7:
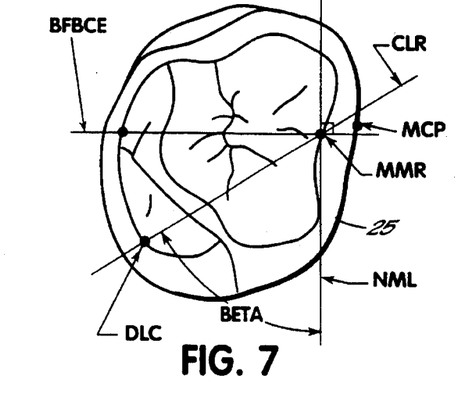
FIG. 7 is a plan diagram illustrating the parameters for placing the maxillary second molar in accordance with a preferred embodiment of the invention.
Figure 8:
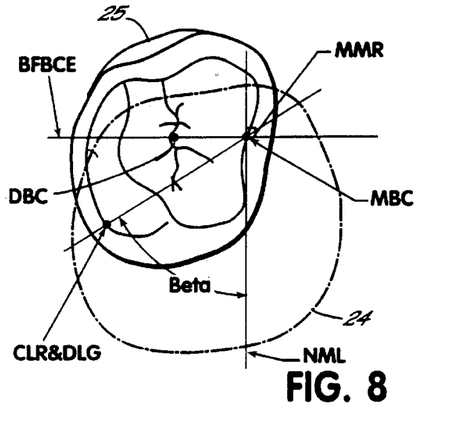
FIG. 8 is a second molar occlusalgram illustrating the relationship of the molars of FIGS. 6 and 7.

The next step is to place the maxillary second molar 25 into its arch. Referring to FIG. 7, (122) line CRL between the mesial marginal ridge MMR and the disto lingual cusp DLC of the upper second molar 25 is constructed for the tooth. The mesial marginal ridge MMR is placed onto the BFBCE. Next, a line NML normal to the BFBCE through the mesial marginal ridge MMR is constructed for the tooth. The maxillary second molar 25 is then rotated about its mesio marginal ridge and translated along the BFBCE until the line CRL between the mesial marginal ridge MMR and the disto lingual cusp DLC is at the angle BETA to line NML and the mesio contact point MCP of the tooth is positioned appropriately, in contact with the first molar 20. The resultant occlusalgram is illustrated in FIG. 8.

Figure 9:
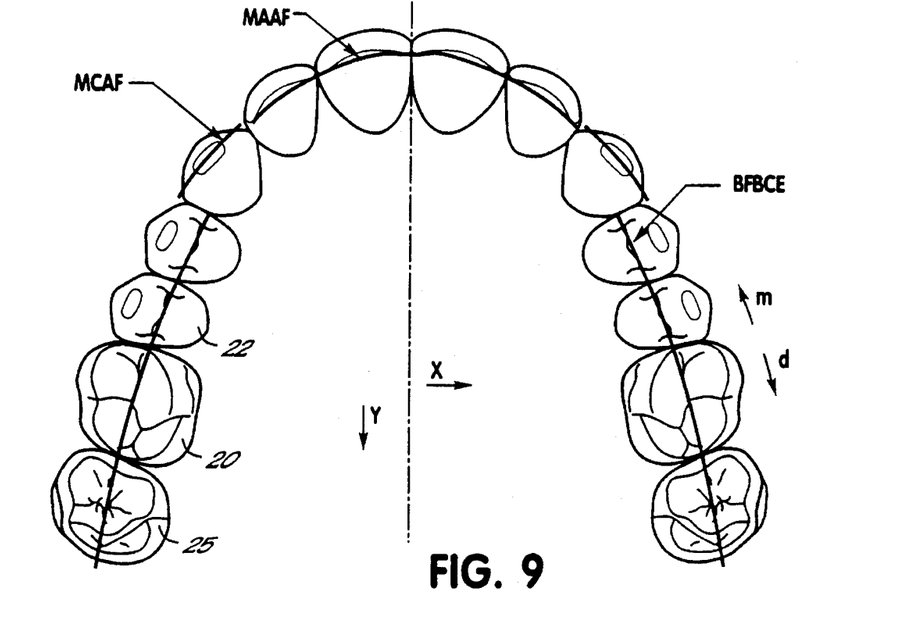
FIG. 9 is a diagram illustrating the maxillary arch of teeth positioned according to the preferred embodiment of the invention.
Figure 10:
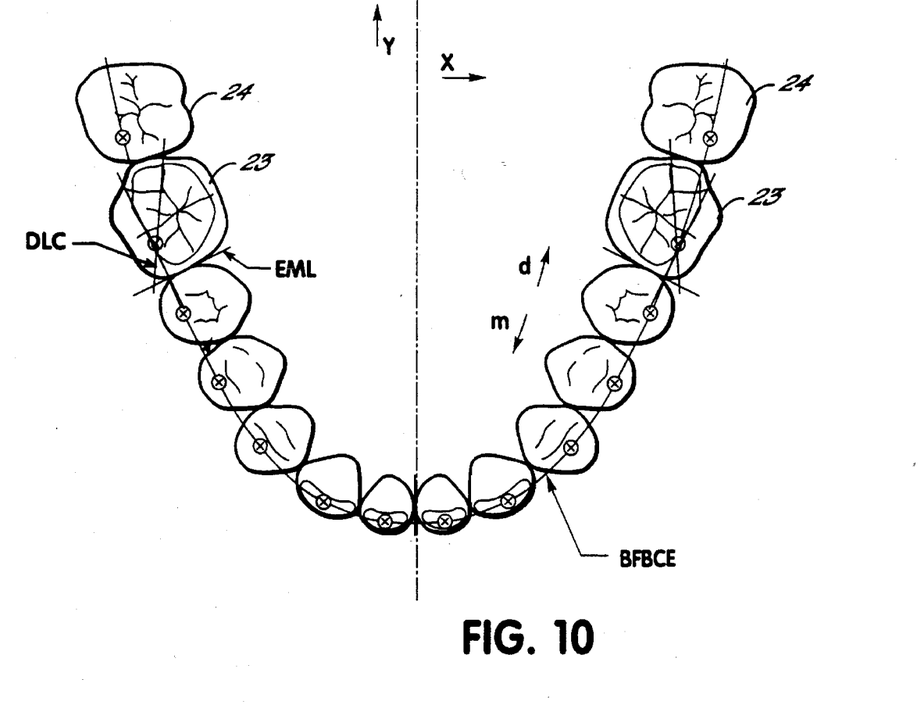
FIG. 10 is a diagram illustrating the mandibular arch of teeth positioned according to the preferred embodiment of the invention.

This completes and relates the maxillary and mandibular dentition. At this point the occlusion has been digitally fit together as an ideal setup independent of brackets, archwires, buccal tubes and positioning jigs. The finish positions of the upper teeth upper teeth are illustrated in FIG. 9. The finish positions of the lower teeth are illustrated in FIG. 10.

Next, (140) the geometries of the brackets 30 and archwires are defined, preferably as set forth in the parent application that is incorporated by reference herein. In the course of the appliance design, bracket geometries are established for each tooth that include the depth of the slot, the torque angle and tip angles for each slot, and a bracket placement position on the corresponding tooth at which the bracket 30 is designed to attach. Included in these geometric properties are a bracket placement height, or distance from the highest prominence of the tooth at which the bracket 30 is to be attached and a bracket base curvature that is designed to conform the mounting base of the bracket to the curvature of the tooth at the bracket attachment point. The slot depth is, more particularly, defined in terms of an in-out dimension or distance, measured in the archwire plane perpendicular to the tooth at the bracket attachment point. This slot depth is the distance from the centerline of the archwire and the surface of the tooth to which the bracket is attached. In addition, the geometries may include a slot rotation angle by which the bottom of the slot of the bracket is sloped relative to the tooth surface at the bracket attachment point so that it is parallel to the archwire at the point of contact between the archwire and the bracket. While the portions of the appliance that connect to the tooth to support the archwire are herein referred to generically as brackets, the term bracket includes not only the single or double wing brackets in which a three sided rectangular slot with one open side is formed in the wings but the tubular type wire support in which the slot is closed and bounded on four sides and commonly referred to as a buccal tube.

A criterium in design of appliance geometry is to define an appliance which has an archwire that is as smooth as possible and lies as close to the teeth as practical. The preferred method of designing the appliance, based either on patient specific or average anatomical data, is the method described in the parent application and in applicants' commonly assigned and copending U.S. application entitled "Low Profile Orthodontic Appliance", filed on even date herewith, hereby expressly incorporated herein by reference. That method includes the establishment of tooth to wire distance limits in the form of a window adjacent each tooth and then calculating the smoothest shaped wires that can pass through all of the windows on the respective upper and lower dental arches. Then the bracket slots are designed to receive such an optimized wire, with the slots formed in the brackets to slot bottoms designed to conform to the shape of the wire.

Calculation of the slot in-out dimensions, the slot rotation angles, and, in the process, the archwire shape is carried out by representing in the computer the cross-sectional shapes of the teeth in the archwire planes, arranged in an arch in their calculated finish positions. Bracket blank geometries are postulated and positioned, in a plan view, in the bracket placement positions on the teeth. Then minimum and maximum in-out dimensions are defined for each tooth in order to insure a sufficient minimum tooth to archwire spacing and to achieve the criteria set to maintain a low profile appliance. Then, an archwire curve is assumed, evaluated for smoothness and compliance with the in-out limits of each of the brackets, and then modified until the criteria for wire smoothness and bracket slot in-out are optimized.

In the appliance design, the brackets 30 and archwires 32 are designed concurrently. This process includes defining for the respective arches, an archwire plane and determining the intersections of the plane with the digitized profiles of the teeth, viewed preferably in the distal direction along the arch. Generally, the mandibular archwire plane is selected to clear, for example by 0.5 min., the maxillary tooth with the maximum overhang, when the teeth are in their calculated finish positions. The upper archwire plane is less constrained and is selected for ease of placement and considerations of gingival health. The intersections of this plane with the profiles of the teeth define the bracket height of the bracket mounting positions of the teeth. The angles of the surfaces of the teeth at the intersection points with the archwire plane define the torque angles of the slots. The tip angles of the slots are determinable based on generally accepted studies.

With lingual appliances, the upper and lower appliance components are reversed in the above description.

This wire and bracket design process is carried out with the in-out dimensions for the molars taken as given seed values to which the other parameters of the appliance mesial of the molars is so optimized. While the above process, which may be considered a computer aided engineering (CAE) process, for design of the appliance is preferred, the resulting design, and a design arrived at according to any other process, produces archwires that will extend adjacent the molars, From such design, the brackets or buccal tubes for the molars, according to the present invention, are designed.

The derivation of the maxillary and mandibular first molar bracket or buccal tube geometries is herein described for the design of buccal tubes, though its applicability to the design of brackets for the molars will be apparent. The same logic, as described above for the teeth mesial of the molars, is utilized to develop maxillary and mandibular first molar buccal tube torque and placement height.

Figure 11:
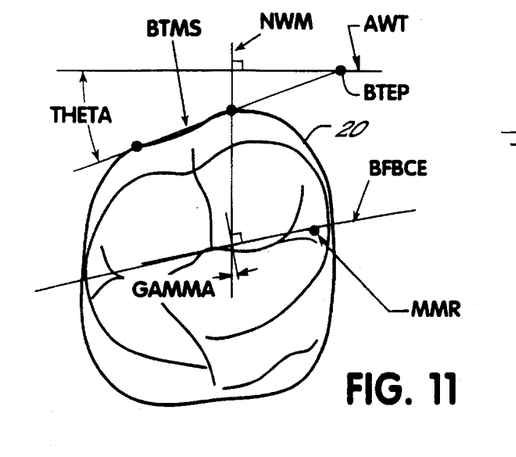
FIG. 11 is a diagram illustrating the development of archwire groove rotation for the maxillary first molar appliance component in accordance with the preferred embodiment of the present invention.

For the design of the appliance referred to above, to determine the rotation or angular offset of a buccal tube for the maxillary first molar 20, (130) a line AWT is constructed tangent to the archwire at a point BTEP, which will correspond to the entrance to a buccal tube, as illustrated in FIG. 11. Next, a line NWM is constructed perpendicular to the archwire tangent line AWT, and the angle GAMMA it makes with the normal to the BFBCE is calculated. The buccal tube mounting surface of the tooth 20 is identified and a line BTMS is constructed parallel to the mounting surface. The angle THETA between the tangent to the archwire equation AWT and the line BTMS describing the buccal tube mounting surface is calculated. The angle THETA is calculated from the BFBCE equation, the angle GAMMA and the digitized tooth shape data for the tooth 20. The angle THETA is the rotation or offset angle required in the maxillary first molar buccal tube.

Figure 12:
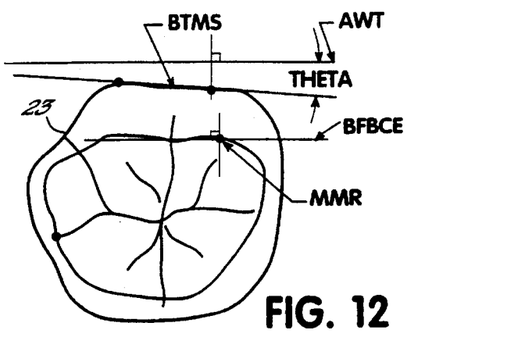
FIG. 12 is a diagram illustrating the development of archwire groove rotation for the mandibular first molar appliance component in accordance with the preferred embodiment of the present invention.
Figure 15:
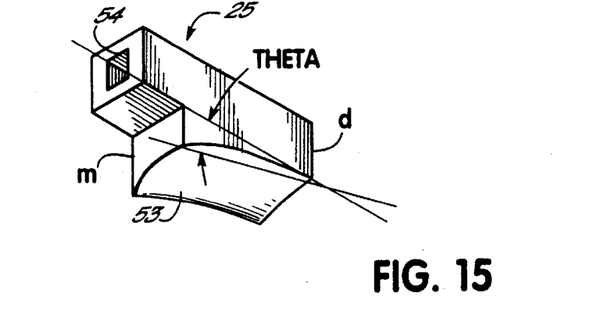
FIG. 15 is a perspective view of a mandibular first molar bracket in the form of a buccal tube embodying principles of the present invention.

To determine the rotation or offset for the buccal tube of the mandibular first molar 23, the procedure is the same as for the maxillary first molar 20, as illustrated in FIG. 12. The buccal tube mounting surface is identified from the digitized tooth shape data and a line BTMS is constructed. The angle THETA between the tangent to the archwire AWT and the line describing the buccal tube mounting surface BTMS is calculated, taking into account the angle GAMMA between the BFBCE and the archwire tangent AWT. The angle THETA becomes the rotation or offset angle required in the mandibular first molar buccal tube 50. According to certain principles of the present invention, this buccal tube for the mandibular first molar, for the standardized version of the appliance, as illustrated in FIG. 15, has a base surface 53 that connects to the mounting surface BTMS (FIG. 12) of the mandibular first molar 23 such that the archwire slot or tube bore 54 it is spaced farther from the tooth at the mesial end m of buccal tube 50 than at the distal end d of the buccal tube 50. Such a buccal tube 50 may be described as mesially rotating the molar relative to the appliance. In Caucasian patients, this rotation angle THETA for the mandibular first molar standardized bracket is preferably 2°, and, for Asian patients, is preferably 4°. In the manufacture of such a bracket 50, up to 2° can be subtracted from THETA where the appliance is used with an archwire that is 1 mill smaller than the buccal tube bore 54, due to factors that tend to rotate the tooth mesially relative to the archwire 32.

Figure 13:
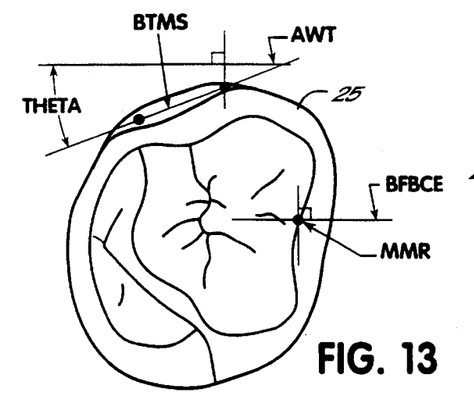
FIG. 13 is a diagram illustrating the development of archwire groove rotation for the maxillary second molar appliance component in accordance with the preferred embodiment of the present invention.
Figure 14:
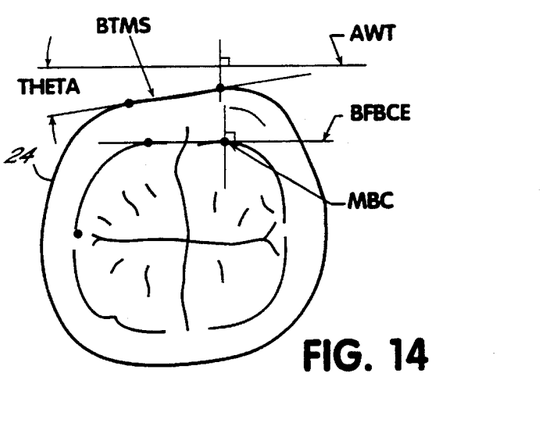
FIG. 14 is a diagram illustrating the development of archwire groove rotation for the mandibular second molar appliance component in accordance with the preferred embodiment of the present invention.

For the derivation of the buccal geometry for the maxillary and mandibular second molars 25 and 24, the same logic, as described above. The maxillary and mandibular first molar buccal tube torque and placement height are developed. Determination of the rotation or offset of the buccal tube for the maxillary second molar 25 is carried out as with the first molars as illustrated in FIG. 13. The buccal tube mounting surface is identified from the digitized tooth shape data and a line BTMS is constructed. The angle THETA between the tangent to the archwire AWT and the line describing the buccal tube mounting surface BTMS is calculated, taking into account the angle GAMMA between the BFBCE and the archwire tangent AWT. This becomes the rotation or offset angle required in the maxillary second molar buccal tube. Similarly, determination of the rotation or offset of the buccal tube for the mandibular second molar 24 is carried out as illustrated in FIG. 14. The buccal tube mounting surface is identified from the digitized tooth shape data and a line BTMS is constructed. The angle THETA between the tangent to the archwire AWT and the line describing the buccal tube mounting surface BTMS is calculated, taking into account the angle GAMMA between the BFBCE and the archwire tangent AWT. This becomes the rotation or offset angle required in the mandibular second molar buccal tube.

Buccal tubes 50 are then fabricated automatically, (160) by converting the geometries calculated as described above into machine codes. The fabrication may be achieved, in the case of buccal tubes, by machining the appropriate torque and rotation angles into the base or support of a buccal tube having a preformed groove therein, to thereby achieve a base rotation angle relative to the groove. Buccal tubes 50 may also be fabricated by custom forming the buccal tube with the appropriately oriented groove. Buccal tubes attached to the supports are secured to a pad for bonding directly to a tooth or are secured to a band that may encircle a tooth and thereby be secured to the tooth. Once fabricated, the buccal tube, or bracket, is preferably positioned on the tooth through the use of a jig. Fabrication of suitable brackets and jigs is described in detail in the parent application.

From the above, particularly the detailed description of the invention, it will be apparent to those skilled in the art that modifications, additions and adaptations of the invention can be made without departing from the principles of the present invention, Accordingly, the following is claimed:

We claim:

1. A method of making an orthodontic appliance for straightening teeth of a patient, the method comprising the steps of:

(1) in a specially programmed digital computer: (a) calculating finish positions of the teeth of the patient based on digitized dental anatomical shape data of the patient, and (b) designing a custom orthodontic appliance to move the teeth of the patient that are mesial to the molars to finish positions on an archform, the appliance including an archwire; and (2) in the computer, (a) calculating archwire position and orientation in the vicinity of the molars, (b) calculating finish positions of the molars that place the molars on the archform; (c) for each of a plurality of the molars, calculating an angle between the calculated orientation of the archwire and a line tangent to the surface of the molar at a connection point thereon when the molar is in its calculated finish position, and (d) for each such molar, calculating the geometry of a bracket for connection to the molar at the connection point thereon, the bracket having a groove therein for receiving the archwire sloped relative to the tooth at a rotation angle approximately equal to the calculated angle; and (3) fabricating each bracket in accordance with the calculated geometry to connect the archwire to the molar at the rotation angle.

2. The method of claim 1 wherein:

step (1) includes the steps of (a) providing machine readable digital records of the shapes of individual teeth representing the teeth of a patient to be treated, (b) determining finish positions to which the teeth of the patient are to be moved by the appliance, (c) calculating, at least in part from the digital records, a digital representation of finish positions of the teeth of a patient, (d) establishing bracket connection points on teeth of the patient anterior of the molars, and (e) deriving, based on the digital records, finish positions and connection points, bracket and archwire geometry of the appliance for connection at the connection points on the teeth anterior to the molars.

3. The method of claim 2 wherein:

step (2)(c) includes the step of calculating, based on the digital records and calculated finish positions of bicuspids, the finish positions of the molars that place (i) the embrasure of the upper first molars perpendicular to an archform on which the bicuspids finish positions are placed with the mesial contact points of the upper first molars in contact with the tooth immediately mesial thereto, and, (ii) the mesial buccal cusp and disto lingual groove of each lower first molar on a line coinciding with a line through the mesial marginal ridge and disto lingual cusp of the upper first molar.

4. The method of claim 1 wherein:

the bracket is a buccal tube having a base with a mounting surface thereon for connection on the appliance connection point of the tooth and an archwire support extending from the base, the groove being formed in the support in the form of a closed bore of uniform cross-section extending therethrough, the bore being sloped relative to the mounting surface in an archwire plane to receive the archwire therein at the rotation angle to the mounting surface.

5. The method of claim 1 wherein:

the bracket is a tie wing bracket having a base with a mounting surface thereon for connection to the connection point on the tooth, the groove therein being an archwire slot in the support, the slot being sloped relative to the mounting surface to receive the archwire therein at the rotation angle to the mounting surface.

6. A orthodontic device for use as part of an orthodontic appliance to connect an orthodontic archwire to a mandibular first molar of a patient, the device comprising:

a support having an archwire groove formed therein to receive and support the archwire axially in the groove;

a base fixed to the support and having a mounting surface thereon configured for mounting at a predetermined connection point on the surface of the molar and for holding the support in a characteristic orientation when the device is mounted to the tooth at the connection point; and the groove being positioned and oriented with respect to the mounting surface of the device to support the archwire at an angle such that, in the mesial direction, the archwire diverges from a line that is generally tangent to the surface of the molar at the connection point, to cause mesial rotation of the molar relative to an archwire supported in the groove.

7. The device of claim 6 wherein:

the device is a buccal tube in which the groove is in the form of a closed bore of rectangular cross-section, the tube being sloped relative to the mounting surface in an archwire plane to receive the archwire therein sloped at the angle of the mesial rotation with respect to the mounting surface.

8. The device claim 6 wherein:

the device is a slotted bracket in which the groove is an archwire slot of rectangular cross-section in the support, and the mounting surface is a bracket base adapted for bonding to the tooth at the connection point, the slot being sloped relative to the mounting surface in an archwire plane to receive the archwire therein sloped at the rotation angle to the mounting surface.

9. The device of claim 6 wherein:

the angle of the mesial rotation is not more than approximately two degrees.

10. The device of claim 6 wherein:

the angle of the mesial rotation is not less than approximately two degrees and not more than approximately four degrees.

11. The device of claim 6 wherein:

the groove has an angle of rotation that is greater than zero in the distal direction and is not more than approximately two degrees less than the angle of the mesial rotation at which the archwire is supported to allow for a distal rotation of an undersized wire in the groove.

12. A method of orthodontic treatment comprising the steps of:

providing an orthodontic appliance component having a groove therein for receiving and supporting an archwire on a tooth of the patient;

securing the component to a mandibular first molar of the patient such that the archwire receiving groove is sloped relative to the tooth at an angle of rotation that will cause the mandibular first molar to assume an angle of rotation, relative to an archwire supported in groove, that is in the mesial direction.

13. The method of claim 12 wherein:

the angle of rotation of the groove is not more than approximately two degrees.

14. The method of claim 12 wherein:

the angle of rotation of the groove is not less than approximately two degrees and not more than approximately four degrees.

15. The method of claim 12 further comprising the step of:

exerting force on such molars through the appliance component to rotate the lower first molar mesially to place the mesial buccal cusp and disto lingual groove thereof on a line coinciding with a line through the mesial marginal ridge and disto lingual cusp of an upper first molar that is has the embrasure thereof perpendicular to an archform of bicuspids and with the mesial contact point thereof in contact with the tooth immediately mesial thereto.

16. A method of making an orthodontic appliance for straightening teeth of a patient, the method comprising the steps of:

providing machine readable digital records of the shapes of individual teeth representing the teeth of a patient to be treated;

defining, in a digital computer, a digital representation of an archform with respect to which the teeth of the patient are to be moved by the appliance;

calculating with the computer, at least in part from the digital records, finish positions of the upper first molars that place the embrasure of each upper first molar perpendicular to the archform and in contact with the tooth immediately mesial thereto;

calculating with the computer, at least in part from the digital records and the calculated finish position of the upper first molars, an angle defining the orientation relative to the archform of a line through the mesial marginal ridge and disto lingual cusp of such upper first molar;

calculating, with the computer, at least in part from the digital records and calculated angle, the finish positions of the lower molars that place the mesial buccal cusps and disto lingual groove thereof on a line parallel the line through the mesial marginal ridge and disto lingual cusp of an occluding upper molar; and fabricating, based on the calculating steps, the orthodontic appliance configured to move the molars to the calculated finish positions.

17. The method of claim 16 wherein:

the lower molar is the mandibular first molar; and the fabricating step includes the fabrication of bracket having a base with a mounting surface thereon for connection at an appliance connection point of the mandibular first molar, the bracket having an archwire support extending from the base and a groove therein formed the support sloped relative to the mounting surface in an archwire plane to receive the archwire therein at the calculated angle to the mounting surface, the angle diverging in the mesial direction so as to rotate the mandibular first molar mesially relative to an archwire supported in the groove.

18. The method of claim 17 wherein:

the bracket is a tie wing bracket having a base with a mounting surface thereon for connection to the connection point on the tooth, the groove therein being an archwire slot in the support, the slot being sloped relative to the mounting surface to receive the archwire therein at the rotation angle to the mounting surface.

19. The method of claim 17 wherein:

the bracket is a buccal tube having a base with a mounting surface thereon for connection at the appliance connection point of the molar, the groove being formed the support in the form of a closed bore of rectangular cross-section extending therethrough, the bore being sloped relative to the mounting surface in the archwire plane to receive the archwire therein at the rotation angle to the mounting surface.

20. A method of orthodontic treatment comprising the steps of:

securing orthodontic appliance components to each of a mandibular first molar and a maxillary first molar of a patient; and exerting force on such molars through the appliance components (i) to move the upper first molar so as to place the embrasure thereof perpendicular to an archform of the bicuspids with the mesial contact point thereof in contact with the tooth immediately mesial thereto, and, (ii) to rotate the lower first molar mesially to place the mesial buccal cusp and disto lingual groove thereof on a line coinciding with a line through the mesial marginal ridge and disto lingual cusp of the placed upper first molar.

\* \* \* \* \*